United States Patent [19]
Durzan et al.

[11] Patent Number: 5,670,663
[45] Date of Patent: Sep. 23, 1997

[54] RECOVERY OF TAXANES FROM CONIFERS

[75] Inventors: Don J. Durzan; Frank Ventimiglia, both of Davis, Calif.

[73] Assignee: Regents of the University of California, Oakland, Calif.

[21] Appl. No.: 601,367

[22] Filed: Feb. 14, 1996

[51] Int. Cl.$^6$ .................................................. C07D 305/14
[52] U.S. Cl. ........................... 549/332; 549/510; 560/248
[58] Field of Search ....................... 549/510, 332; 560/248

[56] References Cited

U.S. PATENT DOCUMENTS 5,547,866  8/1996  Durzan et al. .

OTHER PUBLICATIONS

Sinha et al. (1994) Prog. Drug. Res. 42:53–132.

Guo et al. (1994) Biol. Chem. Hoppe. Seyler, 374(4): 281–7.

*Primary Examiner*—Christina Y. Chan
*Assistant Examiner*—Emma Cech
*Attorney, Agent, or Firm*—Townsend and Townsend and Crew LLP

[57] ABSTRACT

The present invention provides new sources of taxanes and other metabolites from members of the order Coniferales that are not in the genus Taxus.

11 Claims, No Drawings

RECOVERY OF TAXANES FROM CONIFERS

BACKGROUND OF THE INVENTION

The present invention relates to the production and recovery of taxane compounds. In particular, it relates to methods of recovering taxanes from conifer plants other than members of the genus Taxus.

Taxane compounds, in particular paclitaxel (Taxol™), have significant antitumor activity and have been the focus of investigations to develop these compounds as drugs for the treatment of cancer. These compounds have also been shown to inhibit congenital polycystic kidney disease (Woo et al. *Nature* 368 759 (1994)). Paclitaxel, originally isolated from the bark of the Pacific yew, *Taxus brevifolia*, was recently approved by the Food and Drug Administration for use against ovarian cancer and has also shown activity against breast, lung and other cancers.

Continued testing of paclitaxel and other taxanes require quantifies which cannot be obtained from the scarce natural source. *T. brevifolia* is a rare tree, grows slowly, and is not cultivated. In addition, thousands of pounds of bark are required to produce one pound of paclitaxel. Moreover, extraction of the bark is complicated, and product variability occurs.

Because of the scarcity of naturally occurring paclitaxel, numerous investigators have attempted to increase the supply of paclitaxel and other taxanes. For instance, cell suspension cultures of sporophytic tissues have been shown to produce paclitaxel (U.S. Pat. No. 5,019,504). In addition, recent reports describe the total synthesis of paclitaxel (see, Holton et al. *JACS* 116:1597 (1994) and Nicolaou et al. *Nature* 367:630 (1994). These syntheses, however, involve too many steps to be commercially feasible (Flann, *Science* 263:911 (1994)).

Increased availability of taxanes will facilitate investigations to synthesize analogs of paclitaxel or identify other taxanes with similar anti-tumor activity but having improved properties. For instance, paclitaxel is relatively insoluble in aqueous solutions. As a result, paclitaxel is usually dissolved in an oily base of castor oil and alcohol and administered in this form. The identification of related compounds with increased aqueous solubility could provide compounds with better cellular penetration and efficacy than is found with paclitaxel.

Despite advances in the art, availability of paclitaxel and other taxane compounds remains a critical limitation in further investigation and therapeutic use of these compounds. The present invention addresses these and other needs.

SUMMARY OF THE INVENTION

The present invention provides methods of producing taxanes from members of the order Coniferales other than the genus Taxus. The methods comprise contacting the tissue with a composition which extracts taxanes. Any standard method for extracting taxanes may be used. Typically, an organic solvent, such as methanol is used. Any part of the plant may be used as the tissue. Exemplary tissue included bark, cambium, stem, seed, cone, needle, or root tissue. Alternatively, a cell culture derived from the plant may be used. Exemplary genera which may used in the methods include Picea, Fitzroya, Cupressus, and Araucaria.

In some embodiments, the methods include releasing bound taxanes, which are thought to be covalently bound to cell wall and other components and released by, for instance, hydrolysis of the cell wall components. Any method of releasing bound taxanes can be used for this purpose. Typically, the bound taxanes are released by treating the tissue with a glycosidase, such as xylanase.

The invention also provides methods of screening plant tissue from conifer species for the presence of taxanes. The screening method comprise contacting plant tissue or an extract of the plant tissue with an antibody that is specifically reactive with a taxane and detecting the formation of an antigen-antibody complex. Useful antibodies for this purpose include those in TA11, an anti-taxane, rabbit polyclonal serum. Alternatively, monoclonal antibodies such as 3C6, 8A10 and 3H5 can be used. If an extract of the tissue is used, a competitive inhibition enzyme linked immunoassay may be used to detect and quantitate taxane content.

Definitions

The terms "taxanes" refer to compounds comprising the tricyclic ring nucleus shown by

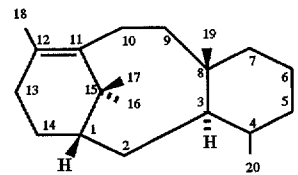

The chemical structure of taxanes and related compounds (e.g., Taxine A) is described in Gueritte-Voegelin *J. Nat. Prod.* 50:9–18 (1987).

Taxanes of the invention can also be identified through the use of monoclonal antibodies raised against paclitaxel and related compounds. A number of such antibodies are known and are commercially available. Suitable antibodies include 3C6, which is specifically reactive with paclitaxel and its C-7 derivatives, and 8A10 which cross reacts with paclitaxel, cephalomannine, baccatin 1II, and 10-deacetylbaccatin III (Kingston et al. *J. Nat. Prod.* 53:1–12 (1990)) and 31–15 which binds with equal affinity to baccatin III and its 7-epi isomer baccatin V. Cross-reactivity studies performed on these various antibodies by Hawaii Biotechnology indicate that the rabbit polyclonal serum recognizes epitopes restricted to the taxane C-13 side chain. Studies with the 3H5 monoclonal antibody indicte that epitope specificity for this antibody encompasses the C-10 through C-13 region of the molecule. The reactivity pattern for the 8A10 monoclonal antibody suggests a specificity for the C-6 through C-2 region. Further, monoclonal antibody 3C6 binds only those baccatin derivatives with a C-13 side-chain. Compounds used for these cross-reactivity studies include the following: Taxol, 10-Deacetyltaxol, 7-epi-10-Deacetyltaxol, 7-Xylosyl-10-deacetyltaxol, 7-epi-Taxol, Cephalomannine, Baccatin III, Baccatin V, 10-Deacetylbaccatin III, 7-epi-10-Deacetylbaccatin III, Taxotere (docetaxel), 2-debenzoyl-2-(p-trifluoromethylbenzoyl)taxol and 20-Acetoxy-4-deacetyl-5-epi-20,0-secotaxol. These antibodies are all commercially available from the Hawaii Biotechnology Group Inc., Aiea, HI. Taxanes can be further identified by their chromatographic behavior in a "taxane" column and their characteristic UV spectra in the 190 to 600 nm range. Taxane-like activity can be assayed using an in vitro microtubule polymerization assay as described in U.S. Pat. No. 5,019,504.

The term "bound taxanes" refers to taxane compounds produced by a plant cell that are not significantly extracted by standard solvent extraction methods, but are recovered after hydrolysis of plant materials. Without wishing to be constrained by any particular theory, such taxanes are thought to be covalently bound to cell wall and other components and released by, for instance, hydrolysis of the cell wall components. Hydrolysis is typically carried out by enzymatic cleavage. Other methods of releasing bound cell wall components can also be used.

As used herein the term "order Coniferales" is used in the standard taxonomic sense to refer to the taxonomic group of gymnosperms generally having well-defined cones. Members of this order are divided among seven plant families: Pinaceae (including e.g., Pinus, Pseudotsuga, Abies, Picea, and Cedrus), Taxodiaceae (including e.g., Taxodium, Metasequoia, and Sequoia), Cupressaceae (including e.g., Cupressus, Juniperus, Thuja, Calocedrus, and Libocedrus), Araucariaceae (including Araucaria and Agathis), Podocarpaceae (including e.g., Podocarpus, Dacrydium, and Phyllocladus), Cephalotaxaceae (Cephalotaxus), and Taxaceae (including Taxus and Torreya). See, e.g., Lawrence, *Taxonomy of Vascular Plants* (Macmillan Company, 1951).

A "composition capable of extracting taxanes" is any composition, typically an organic solvent such as methanol, which can be used to extract taxanes and related compounds from plant tissues containing such compounds. A number of suitable compositions are known in the art. For instance, U.S. Pat. No. 5,445,809 describes the isolation of taxanes using a "reactor compound" containing paclitaxel precursors. U.S. Pat. No. 5,440,055 describes the use of "CoNC fluids" as solvents. As defined in that patent CoNC fluids are comprised of materials which exist as gases at ambient conditions, such as the gases carbon dioxide and nitrous oxide. When such gases are compressed and brought to conditions near or above their critical pressures and temperatures, such gases exhibit enhanced solvating power.

The phrase "specifically reactive with", when referring to the interaction between an antibody and an antigen, such as a taxane ring, refers to a binding reaction between the antigen and the antibody which is determinative of the presence of the antigen in the presence of a heterogeneous population of other compounds. Thus, under designated immunoassay conditions, the specified antibodies bind to a particular antigen against which they were developed and do not bind in a significant amount to other compounds present in the sample.

DESCRIPTION OF THE PREFERRED EMBODIMENT

The present invention provides new sources of taxanes from plants other than members of the genus Taxus. It has been found that a number of genera in the order Coniferales produce significant amounts of taxanes and are therefore good sources of taxanes.

Standard methods for the isolation of taxanes and related compounds from Taxus tissues can be used. The particular method used to extract taxanes and related compounds is not critical to the invention. Typically, taxanes are extracted with organic solvents from the particular plant tissue and chromatographically purified. Adsorbent beads may be used to remove the taxanes produced. In addition, particulate matter released by the cells may be used to adsorb the taxanes. The particular adsorbent material is not a critical aspect of the invention, so long as the material provides a sink for removing the end-product from the reaction sequence.

The extraction process typically begins by contacting the tissue to be extracted with an alcohol (e.g., methanol) at elevated temperature, 50° to 55° C. The extract is then concentrated in methanol. Next, the concentrated methanol extract is partitioned between methylene chloride and water. The methylene chloride fraction, containing paclitaxel, is concentrated. The methylene chloride concentrate is dissolved in 50/50 acetone:hexane, and the mixture is filtered to remove insolubles.

The taxanes are then purified from the acetone:hexane mixture using a variety of chromatographic methods. For instance, the purification of paclitaxel is typically carried out using chromatography on Florisil columns in a 70/30 hexane:acetone mixture to separate the paclitaxel containing fractions. The paclitaxel fractions are then concentrated to dryness. Paclitaxel concentrates are crystallized from a methanol:water mixture and then recrystallized from an acetone:hexane mixture yielding 85 to 95% pure paclitaxel. The paclitaxel is then chromatographed on silica gel with either 2.5% isopropanol or 2.5% n-butanol in methylene chloride to yield approximately 98% pure paclitaxel.

The present invention also provides methods of screening plant tissues for the presence of taxanes and related compounds. Such methods typically involve a competitive inhibition enzyme immunoassay (CIEIA) using an anti-taxane antibody as described above. 8A10 is particularly useful for this purpose because it is specific for a common epitope of the tetracyclic taxane nucleus and is known to be capable of detecting the compounds listed in Table 1.

TABLE 1

| | Taxane | $IC_{50}$ nanomolar |
|---|---|---|
| 1. | paclitaxel | 7 |
| 2. | 10-deacetyltaxol | 10 |
| 3. | 7-epi-10-deacetyltaxol | 15 |
| 4. | 7-xylosyl-10-deacetyltaxol | 17 |
| 5. | Cephalomannine | 8 |
| 6. | baccatin III | 12 |
| 7. | baccatin V | 10 |
| 8. | 10-deacetylbaccatin III | 21 |
| 9. | 7-epi-10-deacetylbaccatin III | 27 |

Note:
$IC_{50}$ = The concentration of analyte required for 50% inhibition of binding of the antibody to the solid phase antigen in CIEIA In some embodiments, tissue cultures derived from the plant tissue of interest are established. Methods for establishing and maintaining plant tissue cultures are well known in the art (see, e.g., P. R. White, 1954, *Cultivation of Animal and Plant Cells* Ronald Press, New York). Typically, the plant material is surface-sterilized prior to introducing it to the culture medium. Any conventional sterilization technique, such as chlorinated bleach treatment can be used. In addition, antimicrobial agents may be included in the growth medium. Under appropriate conditions plant tissue cells form callus tissue, which may be grown either as solid tissue on solidified medium or as a cell suspension cells in a liquid medium. Metabolic products of the callus, such as taxol or other alkaloids, may be isolated from the callus cells or from the culture medium using known techniques (see, e.g., U.S. Pat. No. 5,019,504).

A number of suitable culture media for callus induction and subsequent growth on aqueous or solidified media are known. Exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art (see, e.g., *Plant Cell Culture*, Dixon, ed. IRL Press, Ltd. Oxford (1985) and George et al., *Plant Culture Media*, Vol 1, Formulations and Uses Exegetics Ltd. Wilts, UK, (1987)). For the growth of conifer cells, particularly suitable media include ½ MS, ½ L.P., DCR, Woody Plant Medium (WPM), Gamborg's B5 and its modifications, DV (Durzan and Ventimiglia, *In Vitro Cell Dev. Biol.* 30:219–227 (1994)), SH, and White's medium.

Taxanes, referred to here as "bound taxanes" can also be located on the surfaces of various plant cells and tissues. Enzyme treatment of exhaustively extracted tissues yields taxanes that are detectable by HPLC. By contrast, the nonenzymatically treated controls do not yield detectable taxanes. The present invention also provides extraction methods for the recovery of these bound materials. For a description of methods suitable for this purpose see, Durzan and Ventimiglia, *In Vitro Cell Dev. Biol.* 30:219–227 (1994).

The bound compounds left behind by standard extraction methods provide an extended pool that increases the diversity of known taxanes and their precursors. This diversity is a source for potentially new and novel antitumor compounds and/or their synthons. The enzymatically released compounds show an enhanced solubility in polar solvents. Enhanced solubility in polar solvents, in particular aqueous solutions, provides better cellular penetration and pharmaceutical efficacy than is found in the relatively insoluble paclitaxel.

Additionally, enzymatic treatment of taxane productive sources provides digestion products that are useful as catalytic surfaces and elicitors of further taxane production. Protoplasts derived from cells and tissues with digested cell walls are a source of genetically alterable cells that enable the design of genetically superior lines and potentially taxane productive plant products.

The recovery methods of the invention typically use enzymatic cleavage to release bound taxanes. Exemplary enzymes for this use include glycosidases such as pectinase, xylanase, cellulase and the like. Such enzymes are commonly used to digest cell wall components for the production of protoplasts. Other degradative enzymes known to those of skill in the art, such as lignases, chitinases and the like, can also be used. Other compounds or conditions suitable for the cleavage of chemical bonds in the cell wall or other components of the cell can also be used for this purpose. Suitable methods include the use of strongly oxidizing conditions, acid or alkaline hydrolysis (using either mild or harsh conditions) and the like. Alternatively irradiation or heat can be used to release the compounds.

The methods used to release bound taxanes may in some cases result in artifactual alteration of the chemical structure of the purified taxanes (see, e.g., Miller *J. Nat. Prod.* 43:425 (1980)). Such alterations can be useful as a source for taxanes with improved chemical and pharmaceutical properties, such as solubility, activity, metabolic half-life and the like. These compounds can also be used as synthons for the synthesis of new taxanes.

Enzymes (e.g. cellulase, pectinase and xylanase) as reagents in "live" cultural conditions, whether continuous or batch, can be used to remove bound taxanes and related alkaloids. The released taxanes con then be isolated by extraction. The enzymatic release of other potential substrates into the culture medium would affect synthesis with a positive or negative effect on total yield. Hence, enzymes can be used for process control (feedforward or feedback) of taxane and related alkaloid production. This can be used to manipulate the culture environment to optimize for rapid growth or maximum yield of desired compounds.

The following examples are intended only to further illustrate the invention and not intended to limit the scope of the invention which is defined in the attached claims.

EXAMPLE 1

This example provides evidence that taxanes can be isolated from a number of conifers that are not member of the genus Taxus.

Cells of *Araucaria angustifolia* tissue culture material (cultures were initiated with seeds from Santa Catarina, Brazil), 2) *Fitzroya cupressoides* (seeds and cloned saplings from Valdivia, Chile) and 3) *Cupressus sempervirens* (seeds from Florence, Italy) were treated with antibodies specific for the taxane ring as described in Durzan and Ventimiglia (1994), supra.

Briefly, the immunoassays were carried out as follows. The sample was rinsed in pH 7.0 Tris buffered saline (TBS) for several minutes and then reacted with the primary antibody (anti-mane rabbit antiserum, lot 002, by Hawaii Biotechnology Group) in TBS or with TBS only for 1 to 2 hours at 37° C. The selected anti-taxane antibody (primary antibody) preparation was diluted to an appropriate level as determined by testing. The sample was rinsed in TBS 3 times and treated with the secondary antibody (anti-rabbit IgG, whole molecule, Sigma Chemical Co., St. Louis, Mo.) in TBS or with TBS only for 45 minutes to 1.5 hours at 37° C. The secondary antibody is a selected anti-primary antibody conjugated to an appropriate label such as fluorescein isothiocyante (FITC) or colloidal gold. The sample was rinsed in TBS twice and mounted in Vectashield mounting medium, H-1000 (Vector Laboratories, Burlingmame, Calif.) for fluorescence microscopy (Zeiss fluorescence filter set 48 77 09, ex: 450–4490 nm, em: ≦520 nm).

Strong positive reactions were observed in all samples as compared to controls.

The occurrence of taxane and taxane-related compounds in conifers of a number of genera (Table 2) was confirmed by competitive inhibition of enzyme linked immunoassay (CIEIA) of methanolic extracts (Tables 3–4), as well as by high performance liquid chromatography (HPLC). Methanolic extracts were prepared as outlined in Durzan and Ventimiglia (1994), supra.

TABLE 2

| | |
|---|---|
| *Taxus cuspidata* | Needles and twigs (Positive control) |
| *Araucaria excelsa* | Whole branch + needles |
| *Araucaria angustifolia* | Tissue culture material |
| *Fitzroya cupressoides* | Branch + needles |
| *Picea abies* | Tissue culture material grown on ½ LP medium* |
| *Picea abies* | Tissue culture material grown on ½ LP medium supplemented wth 100 mg/liter colchicine (col). |
| *Cupressus sempervirens* | Tissue culture material |
| *Araucaria angustifolia* | Bark from a dead tree |

*Von Arnold J. Plant physiol. 127:233-244 (1987).

CIEIA was performed blind using the monoclonal antibodies 3C6, 8A10, and 3H5 by Hawaii Biotechnology Group. The assay is based on the concentration of analyte required for 50% inhibition of antibody binding to solid phase antigen ($IC_{50}$).

TABLE 3

| Sample # | Sample I.D. | | Detected Taxane Concentration: ug/ml |
|---|---|---|---|
| 1. | Araucaria excelsa (branches) | a) | 1.7 |
| | | b) | 1.35 |
| | | c) | 0.9 |
| 2 | Araucaria angustifolia (embryo cell cultures) | a) | 0.5 |
| | | b) | 0.75 |
| | | c) | — |
| 3. | Fitzroya (previous year's shoot growth) | a) | 4.4 |
| | | b) | 3.3 |
| | | c) | 1.9 |
| 4. | Picea abies (embryogenic cell cultures) | a) | 0.2 |
| | | b) | 0.3 |
| | | c) | — |
| 5. | Pycea abies (embryogenic cell cultures plus colchicine) | a) | 0.3 |
| | | b) | 0.7 |
| | | c) | — |
| 6. | Cupressus (embryo callus) | a) | 2.5 |
| | | b) | 2.8 |
| | | c) | — |

Note:
Concentration of taxanes determined by reactivity to
a) anti-paclitaxel monoclonal antibody - 3C6
b) anti-taxane monoclonal antibody - 8A10
c) anti-baccatin monoclonal antibody - 3H5
Quantities listed are for the final extract solution µg/ml

TABLE 4

Tissue Concentrations of Taxanes

| Sample # | Sample I.D. | Antibody | ug/KgFW | % of Taxus Production |
|---|---|---|---|---|
| 1. | Araucaria angustifolia (branches) | a. | 62 | 0.062 |
| | | b. | 49 | 0.049 |
| | | c. | 33 | 0.033 |
| 2. | Araucaria angustifolia (embryo cell cultures) | a. | 10 | 0.010 |
| | | b. | 15 | 0.015 |
| | | c. | — | — |
| 3. | Fitzroya (previous year's shoot growth) | a. | 88 | 0.088 |
| | | b. | 66 | 0.066 |
| | | c. | 38 | 0.038 |
| 4. | Picea abies (embryogenic cell cultures) | a. | 10 | 0.010 |
| | | b. | 15 | 0.015 |
| | | c. | — | — |
| 5. | Picea abies (embryogenic cell cultures plus colchicine) | a. | 8 | 0.008 |
| | | b. | 20 | 0.020 |
| | | c. | — | — |
| 6. | Cupressus (embryo callus) | a. | 74 | 0.074 |
| | | b. | 82 | 0.082 |
| | | c. | — | — |

Note:
µg/Kg-FW: micrograms per kilogram of tissue fresh weight or biomass.
Reference:
Taxus produces approximately 100 mg/Kg-FW, about 1000× more than the highest producer in this list. Results show that other trees have the capacity to produce taxanes that are different from paclitaxel.

HPLC was carried out as described in Durzan and Ventimiglia, supra. Briefly, samples were first extracted three times in 100% methanol. A concentrated methanolic extract was mixed with 2 volumes of water and partitioned against methylene chloride twice. The methylene chloride extract was evaporated to dryness. The resulting residue was dissolved in a known volume of 100% methanol and subsequently diluted to 66% with water. This preparation was thoroughly mixed and passed through a 0.22 µm nylon filter before HPLC.

HPLC analysis was performed on 4.3 mm Taxil column (Meta-Chem Technologies, Redondo Beach, Calif.). A 66% methanol isocratic elution with a flow rate of 0.6 ml/min and column temperature of 25° C. was used. Taxane detection (230 nm) and analysis were performed with a Hewlett Packard 1040A diode array spectrophotometer. The results of this analysis indicated the presence of taxanes in all the tissues identified in Table 2.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of producing taxanes, the method comprising contacting plant tissue from a member of the order Coniferales with a composition which extracts taxanes, wherein the plant tissue is not from *Taxus spp*.

2. The method of claim 1, wherein the composition which extracts taxanes is an organic solvent.

3. The method of claim 1, wherein the composition which extracts taxanes is methanol.

4. The method of claim 1, wherein the plant tissue is bark, stem, or needle tissue.

5. The method of claim 1, wherein the plant tissue is from a tissue culture.

6. The method of claim 1, wherein the plant tissue is from Picea.

7. The method of claim 1, wherein the plant tissue is from Fitzroya.

8. The method of claim 1, wherein the plant tissue is from Cupressus.

9. The method of claim 1, wherein the step of producing the taxanes includes releasing bound taxanes.

10. The method of claim 9, wherein the bound taxanes are released by treating the tissue with a glycosidase.

11. The method of claim 10, wherein the glycosidase is xylanase.

* * * * *

UNITED STATES PATENT AND TRADEMARK OFFICE
CERTIFICATE OF CORRECTION

PATENT NO. : 5,670,663
DATED : September 23, 1997
INVENTOR(S) : Don J. Duzan et al.

It is certified that error appears in the above-identified patent and that said Letters Patent is hereby corrected as shown below:

Column 1,
Line 8, kindly insert -- This invention was made with Government support under Grant No. NAG9-825, awarded by the National Aeronautics and Space Administration. The Government has certain rights in this invention. --

Signed and Sealed this

Twenty-eighth Day of June, 2005

JON W. DUDAS
*Director of the United States Patent and Trademark Office*